US011607325B2

(12) United States Patent
Winter, V et al.

(10) Patent No.: US 11,607,325 B2
(45) Date of Patent: Mar. 21, 2023

(54) SHAPE OPTIMIZATION FOR PROSTHETIC FEET

(71) Applicant: Massachusetts Institute of Technology, Cambridge, MA (US)

(72) Inventors: Amos G. Winter, V, Somerville, MA (US); Victor Prost, Rhone-Alpes (FR)

(73) Assignee: Massachusetts Institute of Technology, Cambridge, MA (US)

( * ) Notice: Subject to any disclaimer, the term of this patent is extended or adjusted under 35 U.S.C. 154(b) by 246 days.

(21) Appl. No.: 16/838,208

(22) Filed: Apr. 2, 2020

(65) Prior Publication Data
US 2020/0375763 A1 Dec. 3, 2020

Related U.S. Application Data
(60) Provisional application No. 62/856,394, filed on Jun. 3, 2019.

(51) Int. Cl.
*A61F 2/66* (2006.01)
*A61F 2/76* (2006.01)
*A61F 2/50* (2006.01)

(52) U.S. Cl.
CPC .............. *A61F 2/66* (2013.01); *A61F 2/5046* (2013.01); *A61F 2002/505* (2013.01);
(Continued)

(58) Field of Classification Search
None
See application file for complete search history.

(56) References Cited

U.S. PATENT DOCUMENTS 4,959,073 A * 9/1990 Merlette ................. A61F 2/60
623/27
6,254,643 B1 7/2001 Phillips
(Continued)

FOREIGN PATENT DOCUMENTS

DE 10 2019 100 584 A1 * 7/2020 ............... A61F 2/60
WO WO 2018/218139 A1 11/2018
WO 2020/247052 A1 12/2020

OTHER PUBLICATIONS

Hong Zhou et al., "Shape and Size Synthesis of Compliant Mechanisms Using Wide Curve Theory," Journal of Mechanical Design, vol. 128, No. 3, Jan. 1, 2006, pp. 551-558.
(Continued)

*Primary Examiner* — David H Willse
(74) *Attorney, Agent, or Firm* — Hamilton, Brook, Smith & Reynolds, P.C.

(57) ABSTRACT

A passive prosthetic foot enables a below-knee amputee to walk with near able-body walking motions. The prosthetic foot includes a resilient heel that enables the heel to strike a walking surface more softly than in the prior art and more accurately transition the leg from swing phase to stance phase. The prosthetic foot is modeled generally as a wide Bézier curve, and the foot is characterized according to a set of at least 12 variables, including h, C1d, C2x, C2y, C2d, C3x, C3y, C3d, C4x, C4d, C5d and C6d, where C3y is heel size, C4x is heel geometry and C6d is curve intersection location. The variables are optimized to minimize a difference between a normal lower leg trajectory during gait and a modeled trajectory that includes the prosthetic foot.

35 Claims, 9 Drawing Sheets

(52) U.S. Cl.
  CPC .......... *A61F 2002/5047* (2013.01); *A61F 2002/6642* (2013.01); *A61F 2002/6657* (2013.01); *A61F 2002/6664* (2013.01)

(56) References Cited

U.S. PATENT DOCUMENTS

| | | |
|---|---|---|
| 8,423,167 B2 | 4/2013 | Sanders et al. |
| 9,486,334 B2 | 11/2016 | Tompkins |
| 10,478,121 B2 | 11/2019 | Pusch |
| 11,026,814 B2 | 6/2021 | Klute et al. |
| 2005/0273179 A1 | 12/2005 | Townsend |
| 2007/0021858 A1 | 1/2007 | Slemker et al. |
| 2010/0030343 A1 | 2/2010 | Hansen et al. |
| 2011/0320012 A1 | 12/2011 | Christensen |
| 2016/0063139 A1 | 3/2016 | Cellier et al. |
| 2016/0206447 A1 | 7/2016 | Auberger et al. |
| 2017/0304082 A1 | 10/2017 | Lindhe |
| 2018/0353308 A1 | 12/2018 | Tompkins |
| 2019/0046335 A1 | 2/2019 | Adamczyk |
| 2020/0030121 A1 | 1/2020 | Morales et al. |
| 2020/0085595 A1 | 3/2020 | Winter et al. |
| 2020/0122403 A1 | 4/2020 | Dhokia et al. |

OTHER PUBLICATIONS

European Patent Office, International Search Report and Written Opinion for PCT Application No. PCT/US2020/026308, dated Oct. 26, 2020, 16 pp.

Olesnavage, K.M. et al., "Lower Leg Trajectory Error: A novel optimization parameter for designing passive prosthetic feet," 2015 IEEE International Conference on Rehabilitation Robotics (ICORR), IEEE, Aug. 11, 2015, pp. 271-276.

Xu, D. et al, "Freeform Skeletal Shape Optimization of Compliant Mechanisms," Journal of Mechanical Design, vol. 125, No. 2, Jun. 1, 2003, pp. 253-261.

Filali, M.H., "Prothese du Pied en Materiaux Composites, Öcomposite Material-Based Foot Prothesis," Composites, Plastiques Renforces Fibres de Verre Textile, Centre Doc. Verre Textile Plas Re. Paris, FR, vol. 34, No. 2, Mar. 1, 1994, pp. 62-64.

Winter, D.A., "Biomechanics and Motor Control of Human Movement," John Wiley & Sons, 2009, Appendix A (pp. 296-360).

Howell, L.L., "Compliant Mechanisms," John Wiley & Sons, 2001, pp. 1-3, 12-15, 301-329.

Lan, C.C. et al., "Distributed Shape Optimization of Compliant Mechanisms Using Intrinsic Functions," Journal of Mechanical Design, vol. 130, Jul. 2008, 10 pp.

Hetrick, J. et al., "An Energy Formulation for Parametric Size and Shape Optimization of Compliant Mechanisms," Journal of Mechanical Design, vol. 121, Jun. 1999, pp. 229-234.

International Preliminary Report on Patentability for Int'l Application No. PCT/US2020/026308, titled: Shape Optimization for Prosthetic Feet, dated Dec. 7, 2021.

Össur, "Vari-Flex Catalog," Retrieved from Internet at: https://www.ossur.com/en-us/prosthetics/feet/vari-flex#downloadsContentAnchor, Oct. 30, 2017, (10 pages).

* cited by examiner

SHAPE OPTIMIZATION FOR PROSTHETIC FEET

PRIORITY

This application claims priority from U.S. Provisional Patent Application 62/856,394, filed Jun. 3, 2019, which is incorporated herein by reference in its entirety.

STATEMENT REGARDING FEDERALLY SPONSORED RESEARCH OR DEVELOPMENT

This invention was made with Government support under Grant No. W81XWH-17-1-0427 awarded by the U.S. Army Medical Research and Material Command. The Government has certain rights in this invention.

TECHNICAL FIELD

The present invention relates to passive prosthetic feet and, more particularly, to methods for improving custom passive prosthetic foot designs to enable a user to replicate close-to-normal walking patterns and passive prosthetic feet designed according to such methods.

BACKGROUND

Numerous studies have shown that mechanical design of a passive prosthetic foot affects a user's gait. Several metrics are available for assessing quality of a passive prosthetic foot's design, i.e. how well the foot enables the user to replicate normal lower leg kinematics during gait.

One widely-used metric is roll-over geometry, which is defined as a path of a center of pressure during stance phase, as measured in an ankle-knee reference frame. Roll-over geometry offers advantages over other metrics, in that it can be evaluated for typical physiological walking, providing a target design shape, as well as mechanically for prosthetic feet, without inherent variability of human subjects. However, because roll-over geometry is measured in the ankle-knee reference frame, without including any information regarding the orientation of the ankle-knee reference frame relative to the global reference frame, it is possible for two different prosthetic feet to have identical roll-over geometries, yet exhibit very different lower leg kinematics during gait. Therefore, roll-over geometry is insufficient as a design objective.

Another method, called the Lower Leg Trajectory Error (LLTE), quantifies how closely the position of the lower leg segment of a given prosthetic foot is able to replicate target physiological lower leg positions throughout the course of a step. Two degree-of-freedom architectures have effectively proven the concept of prosthetic foot optimization based on LLTE. However, such devices are generally large, heavy and include relatively complex mechanisms.

PCT Pat. Appl. No. US2018/034628 (published as WO 2018/218139), filed 25 May 2018 by Olesnavage and titled "Method for Design and Manufacture of Compliant Prosthetic Foot" (hereinafter referred to as "Olesnavage"), the entire contents of which are hereby incorporated by reference herein, for all purposes, describes a method for calculating shape and size of a passive prosthetic foot for a below-knee amputee. The Olesnavage passive prosthetic foot (hereinafter referred to as the "Olesnavage foot") enables the amputee to more closely replicate normal walking motions than was previously possible. However, the methodology and passive prosthetic foot suffers from certain problems. A better methodology, and better passive prosthetic feet, are therefore desirable.

SUMMARY OF EMBODIMENTS

An embodiment of the present invention provides a passive prosthetic foot. The passive prosthetic foot includes a generally vertical keel. A generally horizontal elongated forefoot section is attached to the keel at an attachment point. The forefoot section has a toe portion anterior to the attachment point. A resilient heel is attached to the forefoot section posterior to the attachment point. The heel has a stiffness less than about 50 N/mm. At least the keel and the forefoot section are shaped according to a parametric curve characterized by a set of parameters, including at least one of $C_{3y}$, $C_{4x}$, and $C_{6d}$.

Optionally, the set of parameters comprises at least twelve parameters including h, $C_{1d}$, $C_{2x}$, $C_{2y}$, $C_{2d}$, $C_{3x}$, $C_{3y}$, $C_{3d}$, $C_{4x}$, $C_{4d}$, $C_{5d}$, and $C_{6d}$.

Optionally, in any embodiment, the parametric curve includes a wide Bézier curve, a polynomial interpolation and/or a Lagrange function interpolation.

Optionally, in any embodiment, the set of parameters has been optimized to minimize a lower leg trajectory error, relative to a target kinematic data set.

Optionally, in any embodiment, the set of parameters has been optimized taking into consideration an intended user's body weight, height, foot size and preferred walking activity.

Optionally, in any embodiment, the heel is longer than about 0.05 m, longer than about 0.07 m., longer than about 0.10 m., longer than about 0.15 m. or longer than about 0.20 m.

Optionally, in any embodiment, the heel has a stiffness less than about 20 N/mm.

Optionally, in any embodiment, the resilient heel, the shank and the keel are configured to collectively simulate plantar flexion absent an ankle joint.

Another embodiment of the present invention provides a method for fabricating a compliant prosthetic foot. The method includes automatically combining a compliant mechanism optimization technique that includes a set of determinants for a compliant prosthetic foot with a calculation of lower leg trajectory error under a reference loading condition. An optimized set of determinants of the compliant prosthetic foot is automatically formed that minimizes the lower leg trajectory error relative to a target kinematic data set. The compliant prosthetic foot is fabricated in conformance with the optimized set of determinants.

Optionally, in any embodiment, the set of determinants includes at least twelve determinants that include h, $C_{1d}$, $C_{2x}$, $C_{2y}$, $C_{2d}$, $C_{3x}$, $C_{3y}$, $C_{3d}$, $C_{4x}$, $C_{4d}$, $C_{5d}$, and $C_{6d}$.

Optionally, in any embodiment, forming the optimized set of determinants includes taking into consideration an intended user's body weight, height, foot size and preferred walking activity.

Optionally, in any embodiment, the target kinematic data set includes a physiological data set.

Optionally, in any embodiment, the compliant mechanism optimization technique optimizes the set of at least twelve determinants for a prosthetic foot that is compliant along its entire length.

Optionally, in any embodiment, the compliant mechanism optimization technique includes a parameterization step, wherein wide Bézier curve parameters are incorporated into a genetic algorithm to find a set of parameters that creates a foot that minimizes lower leg trajectory error.

Optionally, in any embodiment, the compliant mechanism optimization technique includes a parameterization step, wherein polynomial interpolation curve parameters are incorporated into a genetic algorithm to find a set of parameters that creates a foot that minimizes lower leg trajectory error.

Optionally, in any embodiment, the compliant mechanism optimization technique includes a parameterization step, wherein Lagrange function curve parameters are incorporated into a genetic algorithm to find a set of parameters that creates a foot that minimizes lower leg trajectory error.

Optionally, in any embodiment, the compliant mechanism optimization technique employs a cubic curve defined by relative positions of at least two control points.

Optionally, in any embodiment, the cubic curve is defined by relative positions of four control points.

Optionally, in any embodiment, the compliant mechanism optimization technique employs a width of the Bézier curve as a variable, wherein the width is a function of control circles.

Optionally, in any embodiment, the width of the Bézier curve is defined as a function of diameters of four control circles.

Optionally, in any embodiment, the compliant mechanism optimization technique is combined with the lower leg trajectory error calculation by setting design parameters of the compliant prosthetic foot to not exceed a predefined design space.

Optionally, any embodiment also includes setting the design parameters to limit the design of the compliant prosthetic foot to configurations that are realizable.

Optionally, in any embodiment, the set of determinants of the compliant prosthetic foot is set by finite element analysis.

Optionally, in any embodiment, the finite element analysis includes setting time intervals within a gait cycle and conducting the finite element analysis for each time interval.

Optionally, in any embodiment, the compliant mechanism optimization technique includes employing a resilient heel component in combination with a wide Bézier curve, the resilient heel having a stiffness less than about 50 N/mm.

Optionally, in any embodiment, the time intervals extend from heel strike to toe off, i.e., an entire step.

Optionally, in any embodiment, the target kinematic data set is a physiological data set obtained from a subject for whom the compliant prosthetic foot is being fabricated.

Optionally, in any embodiment, the target kinematic data set is a physiological data set obtained from an able-bodied subject with about the same body size and mass as the subject for whom the compliant prosthetic foot is being fabricated.

Optionally, in any embodiment, the target kinematic data set is a physiological data set scaled from an able-bodied subject to adjust for differences in body size and mass compared to the subject for whom the compliant prosthetic foot is being fabricated.

Optionally, in any embodiment, the target kinematic data set is obtained by at least one member of the group consisting of simulation, measurement of a subject, measurement from a population of subjects and scaling in magnitude from a subject(s) of a different body size and weight.

Optionally, in any embodiment, the compliant prosthetic foot is fabricated by at least one method selected from the group consisting of: machining; three-dimensional printing; a layup method; a water jet method; additive fabrication; subtractive fabrication; lamination; composite manufacture; injection molding; carbon fiber fabrication; extrusion; casting; molding; co-molding; carving; and vulcanization.

Optionally, in any embodiment, the compliant prosthetic foot is fabricated of at least one member of the group consisting of: nylon 6/6; carbon fiber; fiber glass; spring steel; titanium; plastic; an alloy of metals; a polymer; a composite; a resin; a thermoplastic; laminate; a rubber; an elastomer; a non-viscoelastic material; a viscoelastic material; and wood.

Yet another embodiment of the present invention provides a compliant prosthetic foot fabricated by any of the methods described herein.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Embodiments of the present invention enable a below-knee amputee to walk with near able-body walking motions.

Our improvements in these embodiments include a passive prosthetic foot with a resilient heel and improved parameterization of the foot.

Figure 6:
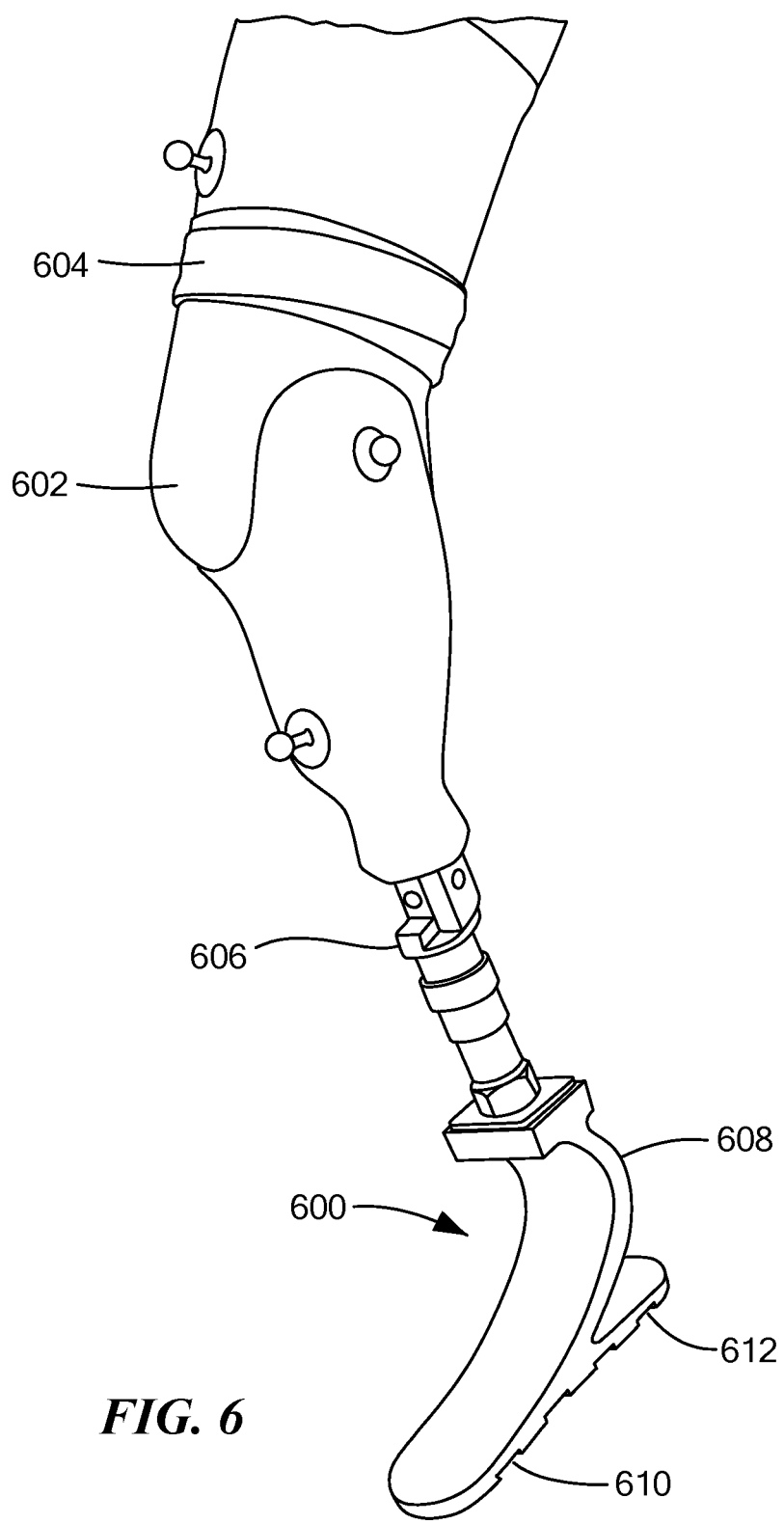
FIG. 6 is an illustration of a below-knee amputee wearing a passive prosthetic foot, according to an embodiment of the present invention.

FIG. 6 is an illustration of a below-knee amputee wearing a passive prosthetic foot 600, according to an embodiment of the present invention. A socket 602 receives a limb stump 604 of the amputee and mechanically connects the limb stump 604, via a shank 606, to the prosthetic foot 600. The foot 600 includes a generally vertical keel 608, an elongated forefoot section 610 and a resilient heel 612 attached to the forefoot section 610.

As used herein, including in the claims, the following terms shall have the following definitions, unless otherwise indicated:

A "compliant mechanism optimization technique" is a means of searching for, identifying and designing a structure for a targeted deflection under a given load. A genetic algorithm, or other optimization technique, may be used to determine the optimized set of determinants.

A "compliant prosthetic foot" is a foot that deforms under load.

A "reference loading condition" is a targeted or anticipated loading that a foot could experience.

An "optimized set of determinants" is a set of variables describing size, form, shape, material and structure of a prosthetic foot in a configuration to provide a targeted deflection under a given load.

In embodiments of the present invention, our passive prosthetic foot includes a resilient heel (such as resilient heel 612 shown in FIG. 6), which solves several problems inherent in prior art feet, such as the Olesnavage foot. The resilient heel enables the heel to strike a walking surface more softly than in the prior art and more accurately transition the leg from swing phase to stance phase. Thus, the heel facilitates close to able-bodied loading and motion. The heel also pushes the main structure of the foot forward more than prior designs, which makes packaging the foot within a physiological envelope easier, thereby making a cosmetic covering easier to fit over the foot.

Embodiments also provide an improved parameterization of prosthetic feet. In some embodiments, we use 12 variables in our parameterization, including heel size ($C_{3y}$), heel geometry ($C_{4x}$) and curve intersection location ($C_{6d}$), which are not used in prior art methodologies. Our parameterization in these embodiments is:

$$X = [h, C_{1d}, C_{2x}, C_{2y}, C_{2d}, C_{3x}, C_{3y}, C_{3d}, C_{4x}, C_{4d}, C_{5d}, C_{6d}]$$

Consequently, we are better able to model the trajectory of the lower leg segment of a prosthetic foot throughout the course of a step. Thus, we are better able to reduce the difference between the trajectory of a prosthetic foot and an able-body walker. This enables us to design a passive prosthetic foot that yields a better Lower Leg Trajectory Error (LLTE) score than previously achievable.

In other embodiments, a subset of the above 12 variables is used in the parameterization of a prosthetic foot. The subset of these variables may include at least one of the heel size ($C_{3y}$), heel geometry ($C_{4x}$), and curve intersection location ($C_{6d}$), which are not used in prior art methodologies. One or more additional variables may be added to the subset of variables. In yet other embodiments, the above 12 variables, along with one or more additional variables, is used in the parameterization of the prosthetic foot.

Figure 1:
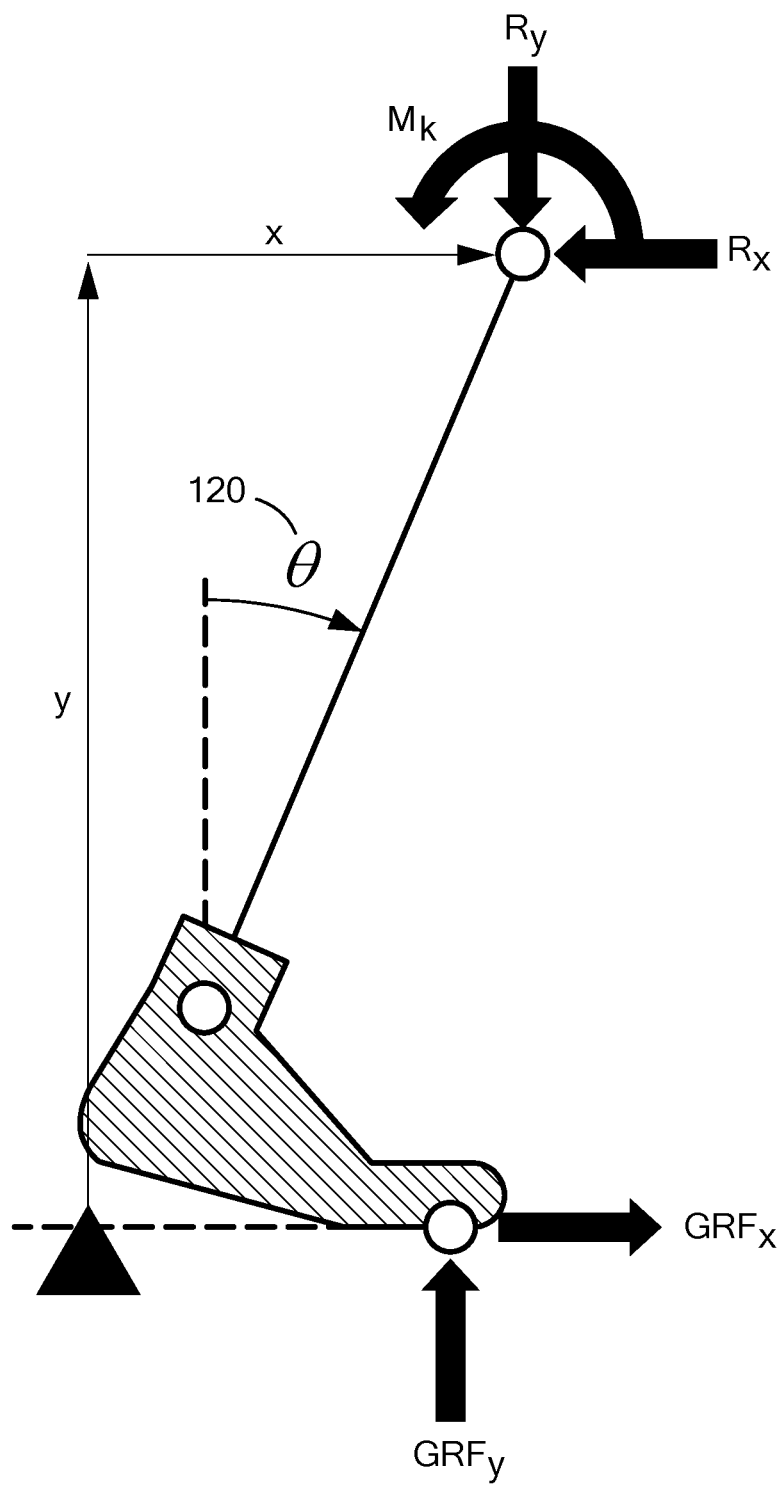
FIG. 1 is a schematic diagram of a simulated residual limb location, calculated from a deformed shape of a foot under a user's body weight, according to the prior art.

For a given prosthetic foot, we can calculate deformation of the foot under a user's body weight during a step (using reference loading data). Force asserted by the user's body weight ($R_x$, $R_y$, and $M_k$) and the resulting ground reaction force ($GRF_x$ and $GRF_y$) is shown in FIG. 1. From the deformed shape of the foot, we then estimate/predict a corresponding trajectory 120 of the user's residual limb (knee/shank, see FIG. 1). By comparing the user's residual limb trajectory 120 to an able-body walker's limb trajectory, we can calculate a performance score, such as the Lower Leg Trajectory Error, for that given prosthetic foot design. The closer the simulated residual limb trajectory is to an able-body walker's trajectory, the better the score for the prosthetic foot design. Using this performance score, we can then tune the geometry and size of the prosthetic foot to yield better performance.

In embodiments of the present invention, we use a parametric model of a foot (see FIG. 2), in which the prosthetic foot is modeled as a parametric shape 200 that defines the prosthetic foot shape. The parametric shape 200 includes a keel 208 and a forefoot section 210. The parametric shape 200 may include a heel. Exemplary suitable parametric shapes include wide Bézier curves, polynomial interpolations and Lagrange function interpolations. Although smooth curves, such as wide Bézier curves, are described, other smooth and non-smooth curves may be used, as long as the curve is elastically deformed upon mechanical loading of a step. A smooth curve is a curve that is a smooth function, where the word "curve" is interpreted in the analytic geometry context. In particular, a smooth curve is a continuous map f from a one-dimensional space to an n-dimensional space which, on its domain, has continuous derivatives up to a desired order. (Wolfram MathWorld.) Thus, a plurality of piece-wise linear segments may be joined, such as end to end, to form the curve. Although a 12-variable parameterization is described for use with a wide Bézier curve, more or fewer variables may be used with other curves, depending on the number of variables required to characterize the curve.

The parametric shape 200 is defined by a series of control points 212, 214, 216, 218. With a Bézier curve, a cubic, or higher-order, curve can be defined by the positions of four control points, reducing a potentially complex shape to a limited number of design variables. The width is added as a variable by using control circles 222, 224, 226, 228, rather than control points, and defining the width of the parametric shape as a function of the diameters of these control circles 222, 224, 226, 228.

In embodiments, we use an optimizer, with our performance score used as the optimizer's objective function, to design a prosthetic foot (find a set of parameters) that enables the user to better replicate normal walking motions. The optimizer may, for example, include genetic algorithm. The goal of the optimizer is to find a foot geometry/structure that would replicate a given walking motion when experiencing loads that a normal person's foot would experience. The foot structure deforms in response to the load to yield the desired walking motion. The desired walking motion may be defined, in terms of loads and motion, to represent walking, jogging, running or any other walking motion the user desires. The optimizer arrives at a design for the foot that best allows the user to do engage in the desired activity. For example, if a user prefers walking slowly, the optimizer uses slow walking motion and loads to design the foot. The foot for each activity would be slightly different, inasmuch as the loads and motion would be different.

Thus, in embodiments the method of designing a prosthetic foot includes a parameterization step, wherein wide Bézier curve, or another parametric curve's, parameters are incorporated into a genetic algorithm to find a set of parameters that creates a foot that minimizes lower leg trajectory error. The minimization may be performed relative to a target kinematic data set of physiological data related to the user. An output of the method may be a 2-dimensional shape. Additional information about wide Bézier curves, parameterization of wide Bézier curves, optimization of the parameters, materials, manufacturing processes, testing and related matters is available in Olesnavage.

Figure 3:
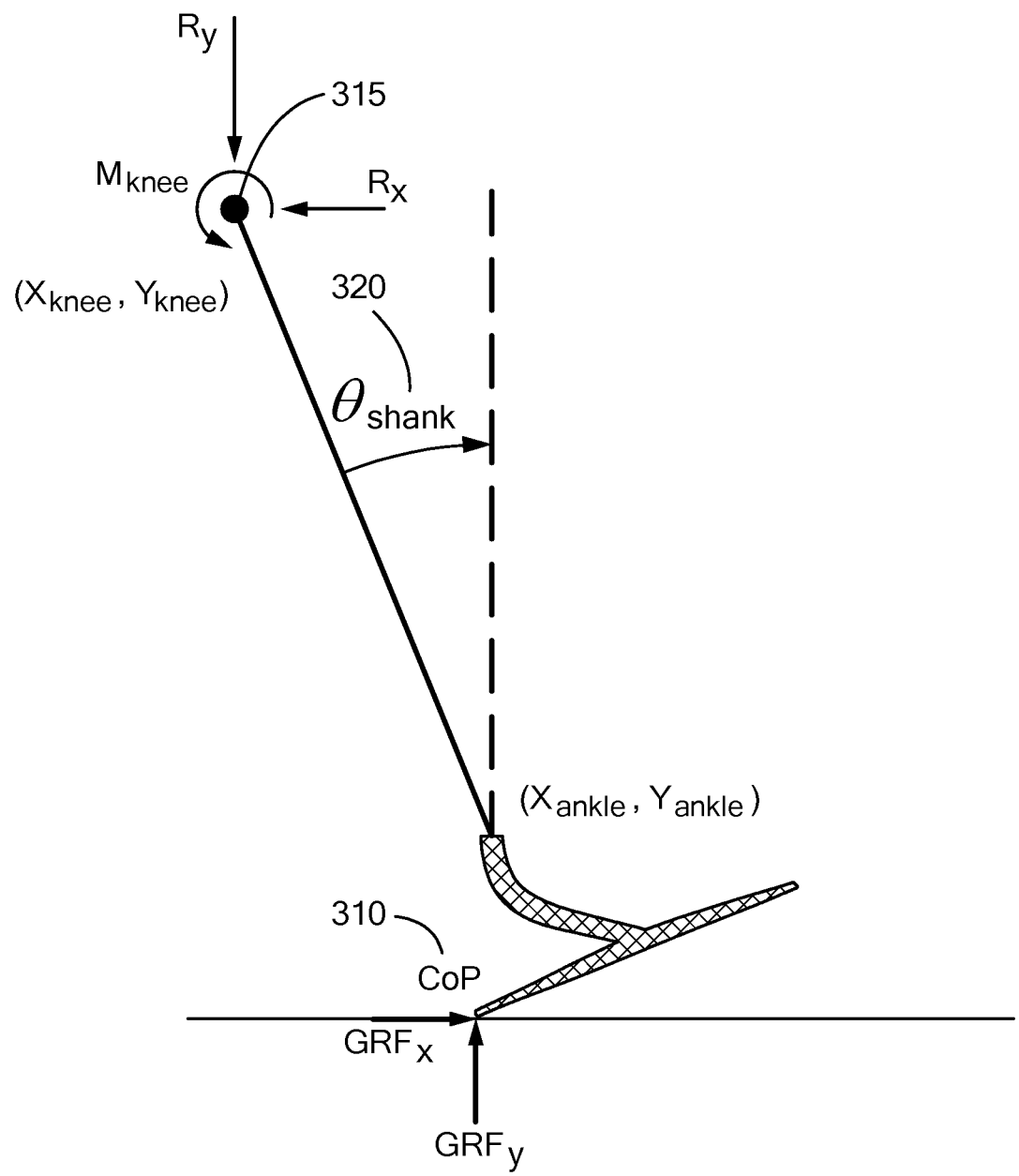
FIG. 3 is a schematic diagram of a simulated residual limb location, calculated during heel strike, according to an embodiment of the present invention.

The process described above actually does not capture the entire complexity of a footstep. At every step, the foot first heel strikes, then rolls to be flat on the ground, before pushing off from the toe to transition to the next step (FIG. 3). The deformed shape of the foot during heel strike and toe-off cannot be accurately calculated by only knowing the user's loading pattern 310 on the ground based on the ground reaction force ($GRF_x$ and $GRF_y$) and center of pressure (CoP). However, from the combined knowledge of the user's loading pattern and the torque ($M_{knee}$) 315 exerted at the user's knee, the deformed shape of the foot during heel strike and toe-off can be calculated (FIG. 3) in embodiments of the present invention. Therefore, in these embodiments, the trajectory 320 of the user's residual limb can be calculated throughout the entire step, not just during foot flat. This enables us to get a more realistic performance score for a given prosthetic foot, since the entire step is taken into account for calculating the performance score.

Figure 4:
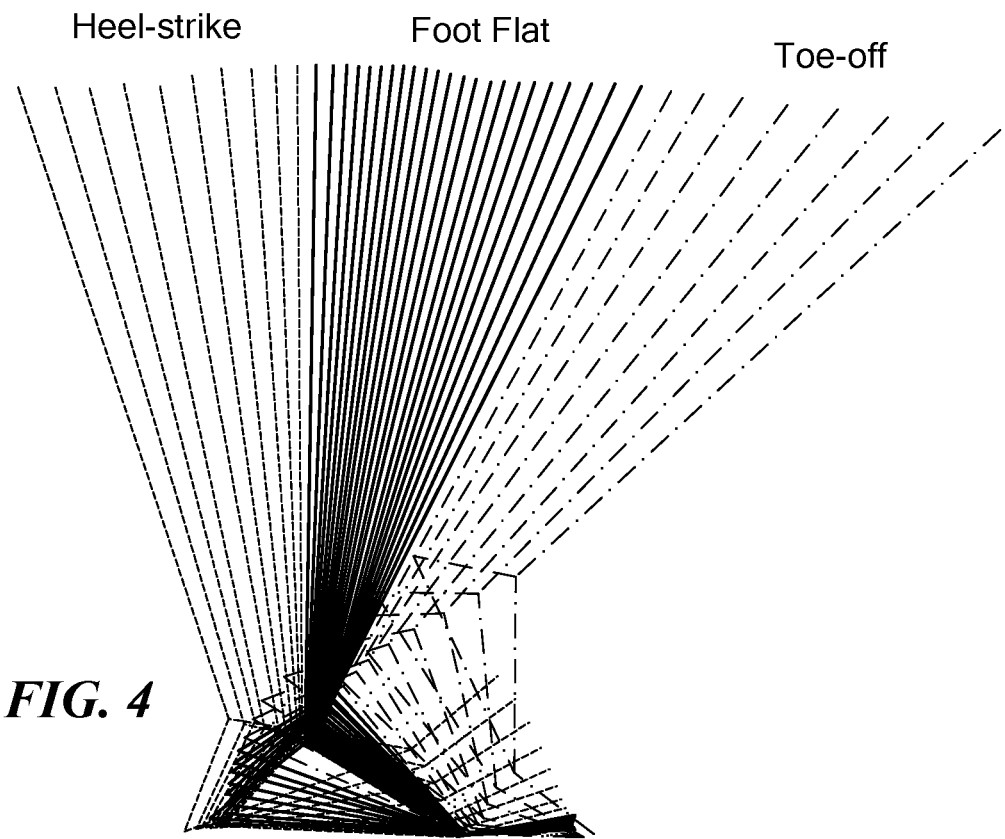
FIG. 4 is a schematic diagram showing three phases during a step, according to an embodiment of the present invention.

Similarly, in embodiments, the parametric model (FIG. 5) was improved to include a resilient heel 212 part of the prosthetic foot. The Olesnavage foot, referenced above, did not include a resilient heel, and the methodology did not take into account a heel. The Olesnavage parameterization included only nine variables, whereas embodiments of our parameterization (FIG. 5) includes 12 variables, including heel size ($C_{3y}$), heel geometry ($C_{4x}$) and curve intersection location ($C_{6d}$), which are not used in prior art methodologies. Furthermore, although Olesnavage used the LLTE metric, Olesnavage modeled only the stance portion of a stride, as evident from number of data points (times) represented in Olesnavage (see FIG. 6 in Olesnavage). Embodiments of the present invention model the entire step, including heel strike and toe-off, as evidenced by a larger number of data points (times) in FIG. 4. Therefore, passive prosthetic feet according to embodiments of the present invention better replicate normal walking motion throughout an entire step, not just when the foot is flat on the ground.

Figure 7:
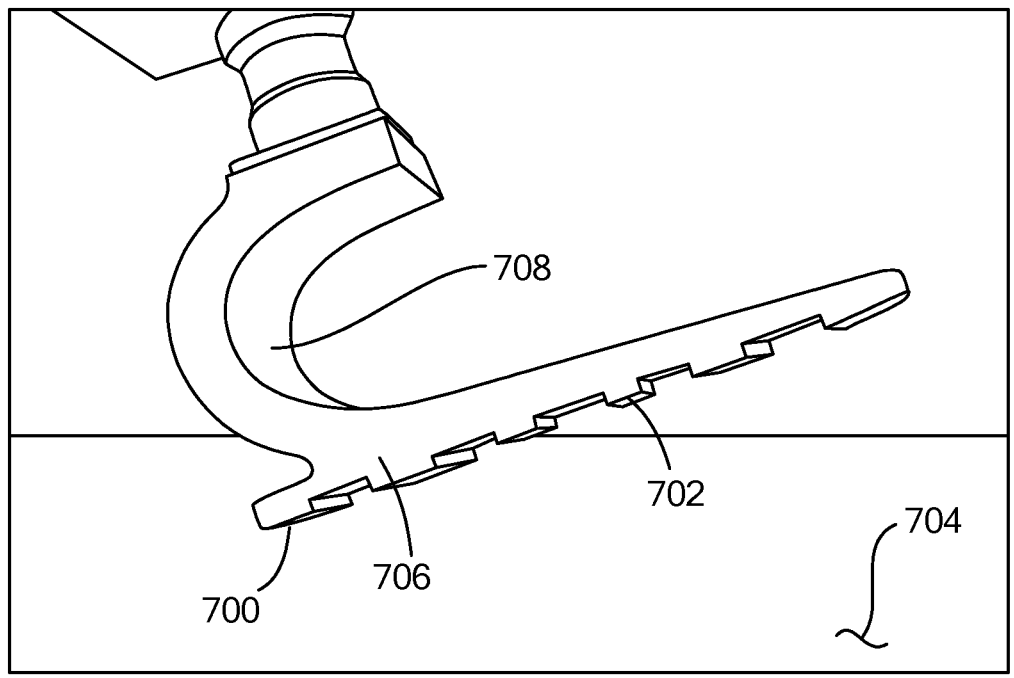
FIG. 7 is side view of a prosthetic foot at heel strike, according to the prior art.

As shown in FIG. 7, the Olesnavage foot includes a keel 708 and a sole 702 at the forefoot section. The Olesnavage foot does not include a resilient heel. The small heel of the Olesnavage foot has a stiffness greater than about 50 N/mm. Consequently, at heel strike, the foot and user experience a shock (sudden force), similar to a heel strike in a stiletto shoe. Furthermore, the foot rotates about a single point 700, i.e., the point of contact between the sole 702 of the foot and the walking surface 704. This single-point rotation makes the foot unstable during heel strike. Furthermore, the user is pushed forward by the mismatch between the foot and normal walking kinematics. The heel stiffness and impact loading cause user discomfort.

Figure 8:
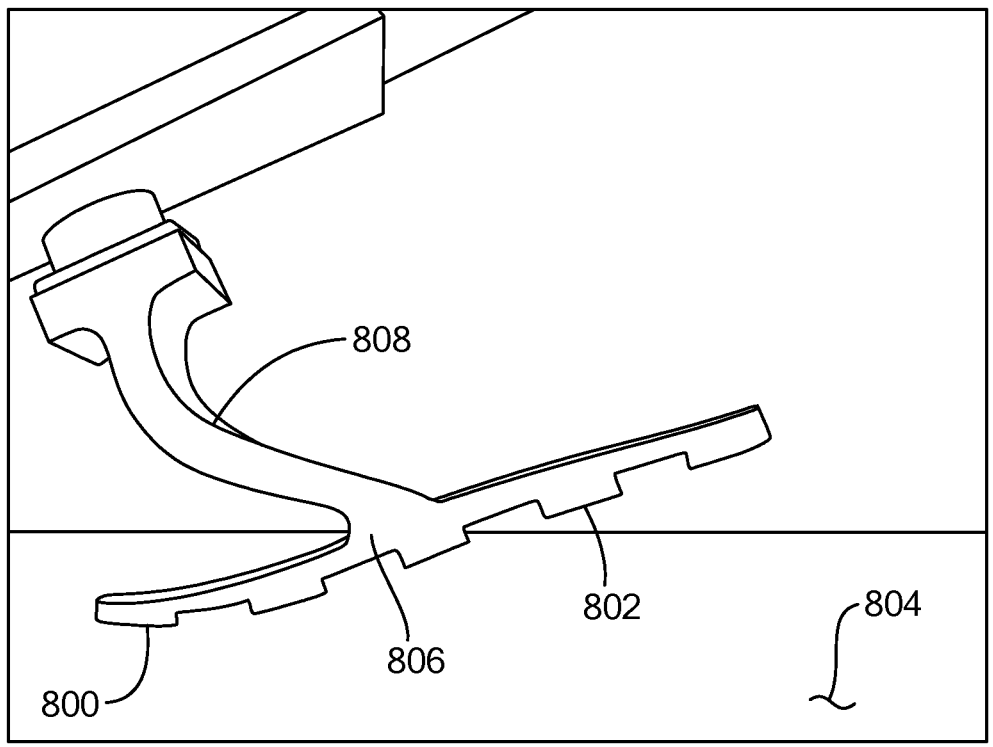
FIG. 8 is a side view of a prosthetic foot at heel strike, according to an embodiment of the present invention.

In contrast, prosthetic feet according to embodiments of the present invention include respective pronounced cantilevered resilient heels 612, exemplified by resilient heel 800 shown in FIG. 8. The resilient heel 800 can have a stiffness of about 5 N/mm to about 100 N/mm. In general, the resilient heel 800 has a stiffness less than about 50 N/mm. According to the embodiment, the resilient heel can be longer than about 0.05 m, longer than about 0.07 m., longer than about 0.10 m., longer than about 0.15 m., or longer than about 0.20 m.

At heel strike, the resilient heel 800 deforms into a convex (as seen from the walking surface 804) curve, and the convex curve rolls over the walking surface 804. This rolling action makes heel strike more stable and comfortable for the user. The thickness of the heel 800 need not necessarily be constant along its length. Instead, the heel thickness can, for example, taper or follow a curve. A heel 800 thickness that varies along the length of the heel can be used to provide a programmed (along the roll of the convex curve) stiffness of the heel 800.

Our analysis shows that LLTE of otherwise similar prosthetic feet is improved by adding the resilient heel 800. For example, in one experiment, the Olesnavage foot (FIG. 7) scored 0.816 LLTE, whereas our foot with a resilient heel 800 (FIG. 8), scored 0.319 LLTE, i.e., an about 60% improvement over the prior art.

Furthermore, the Olesnavage foot (FIG. 7) has a relative short (about 0.05 m) heel, whereas our resilient heel 800 (FIG. 8) in embodiments can be between about 0.02 m and about 0.21 m long. The x axis location of the junction 806 of the forefoot portion 802 and the keel (curved part of the prosthetic foot) 808 in our foot in embodiments is variable ($C_{4x}$, See FIG. 5), therefore the length of the resilient heel 800 is variable. Like the other parameters, the value of $C_{4x}$ for any given prosthetic foot designed by the disclosed methods of the present invention depends on various input values, such as user's body weight and size. In contrast, the Olesnavage heel 700 (FIG. 7) length is fixed. In general, we have found that the junction points 806 in our feet tend to be forward of the junction point 706 in the Olesnavage foot. We have found that this forward placement tends to improve leg kinematics.

Figure 9:
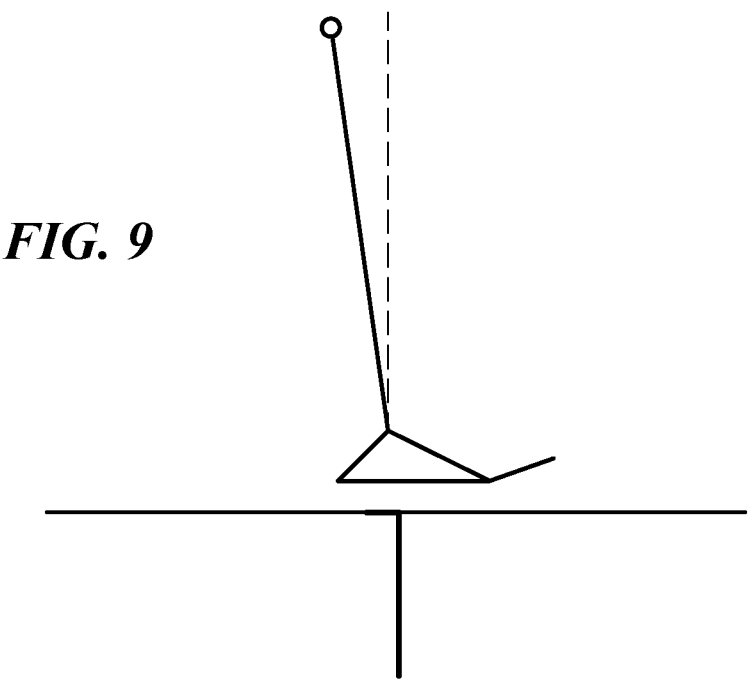
FIG. 9 is a schematic diagram of a passive prosthetic foot with a compliant heel, as in FIG. 8, exhibiting pseudo-plantar flexion at heel strike, according to an embodiment of the present invention.
Figure 10:
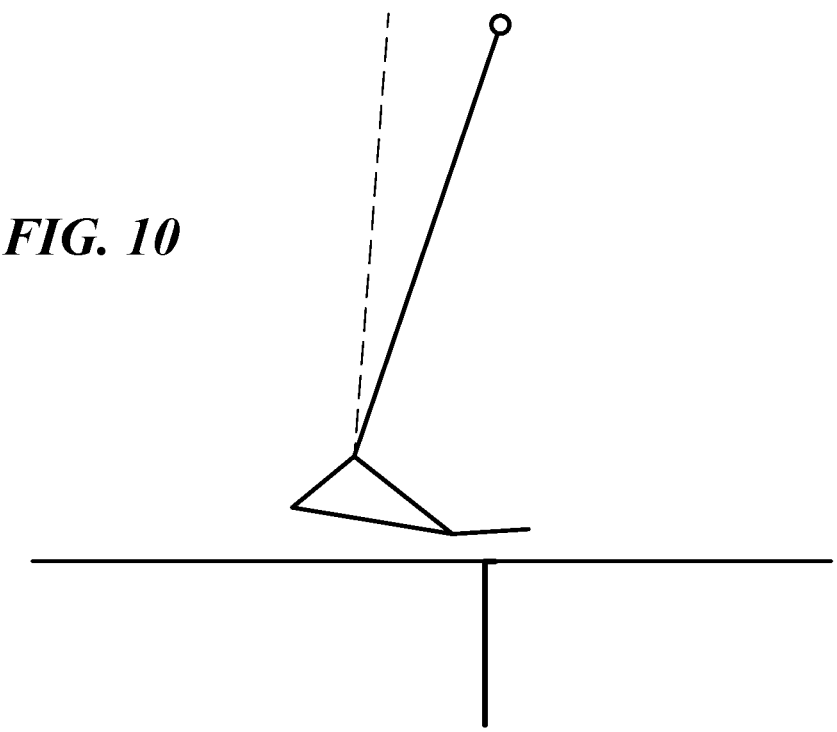
FIG. 10 is a schematic diagram of a passive prosthetic foot with a compliant heel, as in FIG. 8, exhibiting controlled dorsiflexion at mid-stance, according to an embodiment of the present invention.
Figure 11:
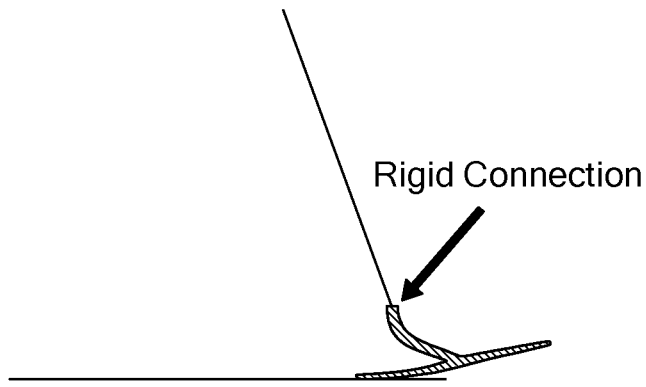
FIG. 11 is a schematic diagram of a passive prosthetic foot with a compliant heel, as in FIG. 8, exhibiting pseudo-plantar flexion as a result of stiffness of a front part of the foot ("toes") being greater than stiffness of the heel part of the foot, according to an embodiment of the present invention.
Figure 12:
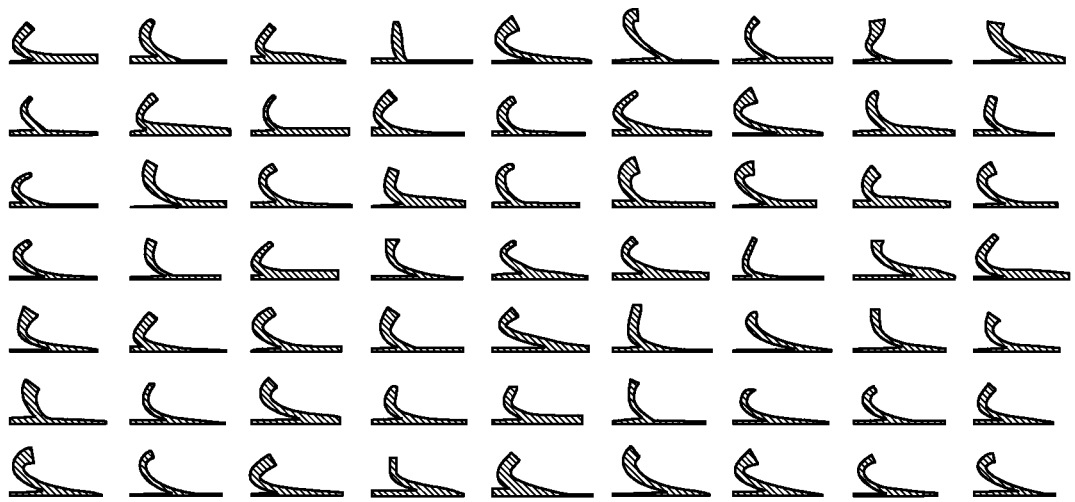
FIG. 12 illustrates side views of sixty-three exemplary keel designs for a passive prosthetic foot, according to respective embodiments of the present invention.

As shown schematically in FIG. 11, in embodiments of the present invention, the stiffness of a front part of the foot ("toes") is greater than the stiffness of the heel part of the foot, which results in pseudo-plantar flexion at heel strike (FIG. 9). In other words, plantar flexion stiffness is less than dorsiflexion stiffness (FIG. 10). In some embodiments, the plantar flexion stiffness is about four times lower than the dorsiflexion stiffness. The resilient heel 800, the keel 808 and the forefoot portion 802 are configured to collectively simulate plantar flexion, without requiring an ankle joint in the prosthetic foot. FIG. 12 shows some exemplary keel designs for the prosthetic foot in embodiments of the present invention.

These new geometries in embodiments of the present invention facilitate the user in replicating able-bodied loading and motion of his/her amputated leg. This improved framework of embodiments of the present invention can be used to design custom prosthetic feet for below-knee amputees, based on an intended user's body weight, height, foot size and preferred walking activity. Geometry of each passive prosthetic foot depends on the intended user's body weight, height, foot size and preferred walking activity. Passive prosthetic feet were designed and tested for below-knee amputees, based on this framework (FIG. 6). This framework yields high-performance prosthetic feet, at a very low cost, and several other benefits over traditional prosthetic design methodologies.

This framework is resource efficient. Traditional prosthetic design methods are based on trial and error and require many engineers and patients studies to achieve a desired prosthetic foot design. This design is then scaled to other patients based on shoe size and weight only. However, not all parameters of a prosthetic food scale linearly. Thus, it usually takes years and many resources to develop a given prosthetic foot, resulting in their very high retail price. Using our framework according to embodiments of the present invention, a prosthetic foot with similar performances can be designed within hours.

Our framework yields tailored prosthetic feet. Our methodology according to embodiments of the present invention yields a design for a prosthetic foot for a specific user's body weight, foot size, height, limb lengths and preferred walking pattern. Thus, different prosthetic feet can be designed for a single intended user, depending on intended walking patterns, ex., walking and running. We can also tailor the performance based on the available resources. For example, expensive materials, such as carbon fiber, can be chosen to yield best available performance, or affordable and/or locally available materials, such as plastics (nylon, urethane, etc.) can be chosen to hold down costs and facilitate local manufacturing or repair, while providing acceptable walking performance scores.

This methodology provides prosthetic feet exhibiting increased fidelity and performance. Using our extended framework to the full step (compared to previous work), we can get a more accurate performance score for each prosthetic foot. In addition, the new parametric model enables us to consider a wider range of possible designs. Combining these two improvements yields better performing/better-optimized prosthetic feet.

This framework facilitates easy manufacturing and packaging completed prosthetic feet. Because each prosthetic foot design is a result of an optimization framework, we can include any manufacturing constraints and foot form/geometry requirements, without any additional cost or resources.

Given the possibilities offered by this framework, high performance, custom prosthetic feet can be provided at an affordable cost for any market, including developed countries and developing countries.

Figure 13:
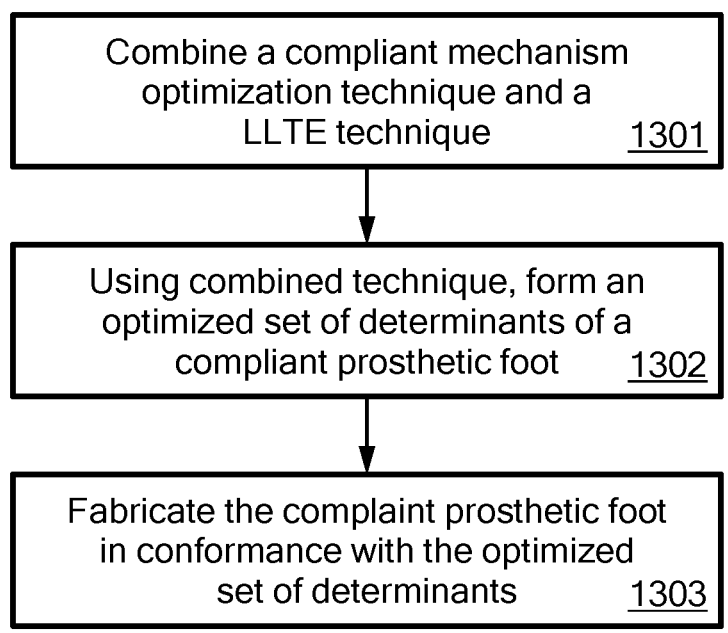
FIG. 13 is a flowchart of a method for fabricating a compliant prosthetic foot, according to an embodiment of the present invention.

FIG. 13 is a flowchart of a method for fabricating a compliant prosthetic foot, according to an embodiment of the present invention. The method begins at step 1301 by combining a compliant mechanism optimization technique that includes a set of determinants for a compliant prosthetic foot (such as described above with respect to FIGS. 2 and 5) with a calculation of lower leg trajectory error under a reference loading condition (such as described above with respect to FIG. 3). In some embodiments, the combination is made by setting design parameters of the complaint prosthetic foot to not exceed a predefined design space.

Figure 5:
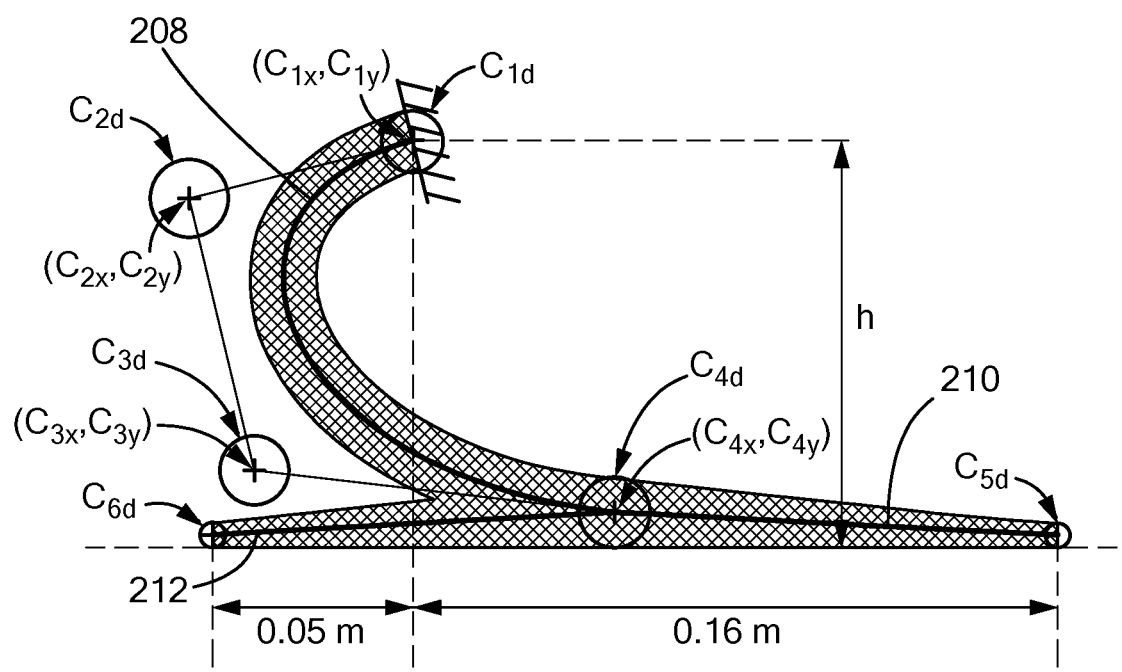
FIG. 5 is a schematic diagram showing a parametric definition of a prosthetic foot with a heel, according to an embodiment of the present invention.

In some embodiments, the set of determinants has at least twelve determinants that include h, $C_{1d}$, $C_{2x}$, $C_{2y}$, $C_{2d}$, $C_{3x}$, $C_{3y}$, $C_{3d}$, $C_{4x}$, $C_{4d}$, $C_{5d}$, and $C_{6d}$ (12 parameterization variables of FIG. 5). In some embodiments, the set of determinants includes at least one of $C_{3y}$, $C_{4x}$, and $C_{6d}$ shown in FIG. 5. In some embodiments, the set of determinants is set by finite element analysis, which may include setting time intervals within a gait cycle and conducting the finite element analysis for each time interval. The time intervals may extend from heel strike to toe off.

Step 1302, using the combined technique, forms an optimized set of the determinants that minimizes the lower leg trajectory error relative to a target kinematic data set. Step 1302 may form the optimized set of determinants by taking into consideration of the subject's body weight, height, foot size and/or preferred walking activity. In some embodiments, the target kinematic data set is a physiological data set obtained from a subject for whom the compliant prosthetic foot is being fabricated, or an able-bodied individual. The able-bodied individual may be about the same body size and weight as the subject, or the data of the able-bodied individual may be scaled to adjust for differences in body size and weight compared to the subject. In other embodiments, the target kinematic data set is obtained using simulation, measurement of the subject, or measurement from a population of individuals and scaling in magnitude the measurements from individual(s) of a different body size and weight.

Figure 2:
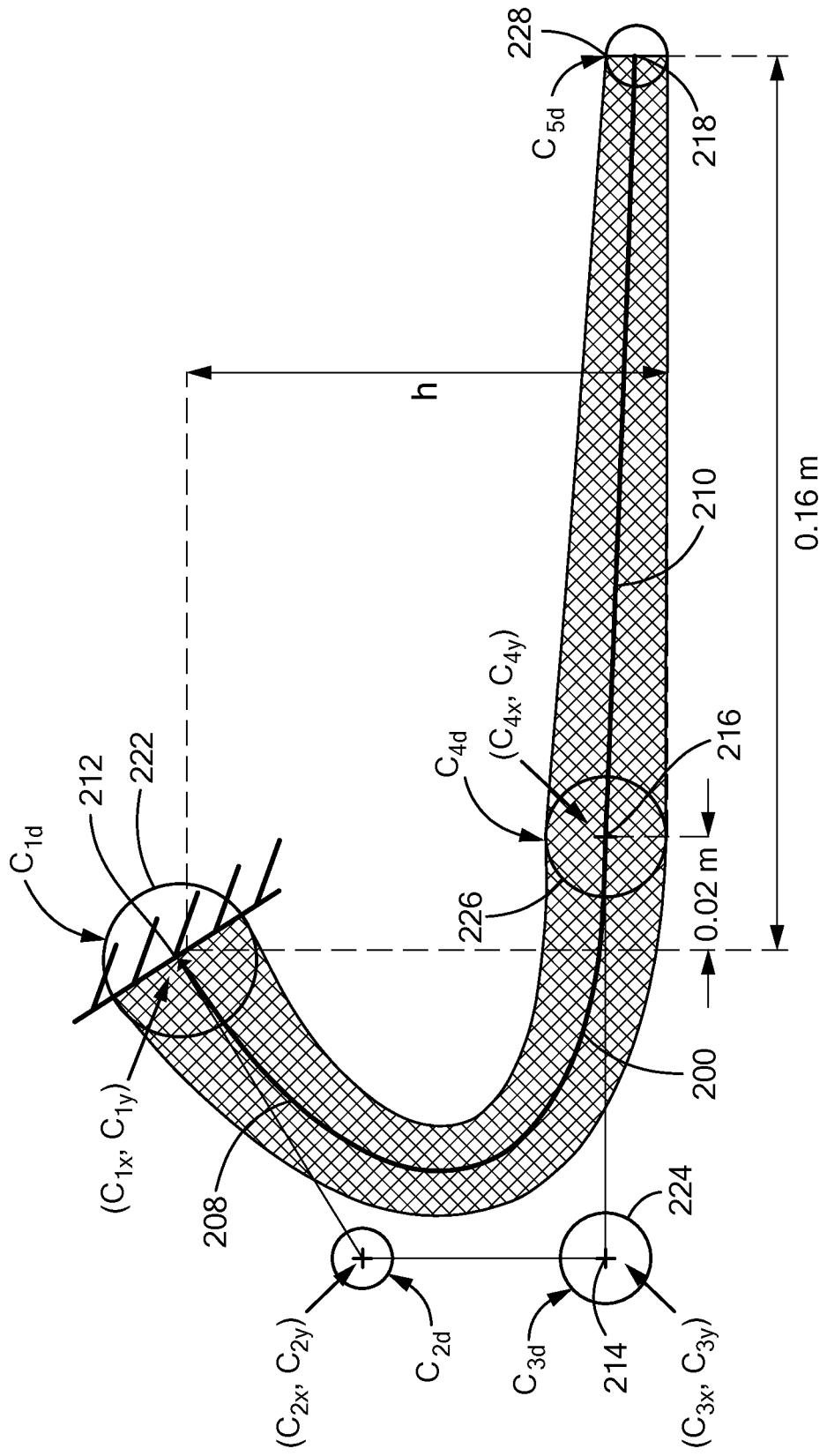
FIG. 2 is a schematic diagram showing a parametric definition of a prosthetic foot, according to an embodiment of the present invention.

The compliant mechanism optimization technique may include a parameterization step, in which Bézier curve parameters, polynomial interpolation curve parameters, Lagrange function curve parameters, or other such parametric curve parameters are incorporated into a genetic algorithm to find a set of parameters that creates a foot that minimizes lower leg trajectory error. In embodiments, the compliant mechanism optimization technique employs a cubic curve defined by relative positions of at least two control points or at least four control points. In embodiments employing the Bézier curve parameters, the compliant mechanism optimization technique employs the width of the Bézier curve as a variable, such that the width is defined as a function of the diameter of control circles, e.g., four control circles, as shown in FIGS. 2 and 5. The compliant mechanism optimization technique optimizes the set of determinants for a prosthetic foot that is compliant along its entire length.

The method, at step 1303, fabricates the compliant prosthetic foot in conformance with the optimized set of determinants. In embodiments, the compliant prosthetic foot is fabricated by machining; three-dimensional printing; a layup method; a water jet method; additive fabrication; subtractive fabrication; lamination; composite manufacture; injection molding; carbon fiber fabrication; extrusion; casting; molding; co-molding; carving; and/or vulcanization. In embodiments, the compliant prosthetic foot is fabricated with nylon 6/6; carbon fiber; fiber glass; spring steel; titanium; plastic; an alloy of metals; a polymer; a composite; a resin; a thermoplastic; laminate; a rubber; an elastomer; a non-viscoelastic material; a viscoelastic material; and/or wood.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof, such as the optimizer, may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective elements from one another and are not intended to indicate any particular order or total number of elements in any particular embodiment. Thus, for example, a given embodiment may include only a second element and a third element.

What is claimed is:

1. A passive prosthetic foot comprising:
a generally vertical keel;
a generally horizontal elongated forefoot section attached to the keel at an attachment point, the forefoot section having a toe portion anterior to the attachment point; and
a resilient heel attached to the forefoot section posterior to the attachment point, wherein:
the heel has a stiffness less than about 50 N/mm;
the heel, the keel and the forefoot section are shaped according to a parametric curve characterized by a set of parameters, including a heel size ($C_{3y}$), a heel geometry ($C_{4x}$), and a curve intersection location ($C_{6d}$), the parametric curve comprising a polynomial interpolation or a Lagrange function interpolation.

2. A passive prosthetic foot according to claim 1, wherein the set of parameters comprises at least twelve parameters including a height of the prosthetic foot (h), and at least one geometric parameter at each of six control points of the parametric curve ($C_{1d}$, $C_{2x}$, $C_{2y}$, $C_{2d}$, $C_{3x}$, $C_{3y}$, $C_{3d}$, $C_{4x}$, $C_{4d}$, $C_{5d}$, and $C_{6d}$).

3. A passive prosthetic foot according to claim 1, wherein the set of parameters has been optimized to minimize a lower leg trajectory error, relative to a target kinematic data set.

4. A passive prosthetic foot according to claim 1, wherein the set of parameters has been optimized taking into consideration an intended user's body weight, height, foot size and preferred walking activity.

5. A passive prosthetic foot according to claim 1, wherein the heel is longer than about 0.05 m.

6. A passive prosthetic foot according to claim 1, wherein the heel is longer than about 0.07 m.

7. A passive prosthetic foot according to claim 1, wherein the heel is longer than about 0.10 m.

8. A passive prosthetic foot according to claim 1, wherein the heel is longer than about 0.15 m.

9. A passive prosthetic foot according to claim 1, wherein the heel is longer than about 0.20 m.

10. A passive prosthetic foot according to claim 1, wherein the heel has a stiffness less than about 20 N/mm.

11. A passive prosthetic foot according to claim 1, wherein the resilient keel, the forefoot section and the heel are configured to collectively simulate plantar flexion absent an ankle joint.

12. A method for fabricating a compliant prosthetic foot, comprising automatically:
a) combining a compliant mechanism optimization technique that includes a set of determinants for a compliant prosthetic foot comprising a heel with a calculation of lower leg trajectory error under a reference loading condition, the set of determinants including a heel size ($C_{3y}$), a heel geometry ($C_{4x}$), and a curve intersection location ($C_6$);
b) forming an optimized set of determinants of the compliant prosthetic foot that minimizes the lower leg trajectory error relative to a target kinematic data set; and
c) fabricating the compliant prosthetic foot in conformance with the optimized set of determinants.

13. A method according to claim 12, wherein the set of determinants comprises at least twelve determinants that include a height of the prosthetic foot (h), and at least one geometric parameter at each of six control points of a parametric curve ($C_{1d}$, $C_{2x}$, $C_{2y}$, $C_{2d}$, $C_{3x}$, $C_{3y}$, $C_{3d}$, $C_{4x}$, $C_{4d}$, $C_{5d}$, and $C_{6d}$).

14. A method according to claim 13, wherein the compliant mechanism optimization technique optimizes the at least twelve determinants for a prosthetic foot that is compliant along its entire length.

15. A method to according to claim 12, wherein forming the optimized set of determinants comprises taking into consideration an intended user's body weight, height, foot size and preferred walking activity.

16. A method according to claim 12, wherein the target kinematic data set includes a physiological data set.

17. A method according to claim 12, wherein the compliant mechanism optimization technique includes a parameterization step, wherein wide Bezier curve parameters are incorporated into a genetic algorithm to find a set of parameters that creates a foot that minimizes lower leg trajectory error.

18. A method according to claim 17, wherein the compliant mechanism optimization technique employs a width of the Bezier curve as a variable, wherein the width is a function of control circles.

19. A method according to claim 17, wherein the width of the Bezier curve is defined as a function of diameters of four control circles.

20. A method according to claim 12, wherein the compliant mechanism optimization technique includes a parameterization step, wherein polynomial interpolation curve parameters are incorporated into a genetic algorithm to find a set of parameters that creates a foot that minimizes lower leg trajectory error.

21. A method according claim 12, wherein the compliant mechanism optimization technique includes a parameterization step, wherein Lagrange function curve parameters are incorporated into a genetic algorithm to find a set of parameters that creates a foot that minimizes lower leg trajectory error.

22. A method according to claim 12, wherein the compliant mechanism optimization technique employs a cubic curve defined by relative positions of at least two control points.

23. A method according to claim 22, wherein the cubic curve is defined by relative positions of four control points.

24. A method according to claim 12, wherein the compliant mechanism optimization technique is combined with the lower leg trajectory error calculation by setting design parameters of the compliant prosthetic foot to not exceed a predefined design space.

25. A method according to claim 24, further comprising setting the design parameters to limit the design of the compliant prosthetic foot to configurations that are realizable.

26. A method according to claim 12, wherein the set of determinants of the compliant prosthetic foot is set by finite element analysis.

27. A method according to claim 26, wherein the finite element analysis includes setting time intervals within a gait cycle and conducting the finite element analysis for each time interval.

28. A method according to claim 27, wherein the compliant mechanism optimization technique includes employing a resilient heel component in combination with a wide Bezier curve, the resilient heel having a stiffness less than about 50 N/mm.

29. A method according to claim 27, wherein the time intervals extend from heel strike to toe off.

30. A method according to claim 12, wherein the target kinematic data set is a physiological data set obtained from a subject for whom the compliant prosthetic foot is being fabricated.

31. A method according to claim 12, wherein the target kinematic data set is a physiological data set obtained from an able-bodied subject with about the same body size and mass as the subject for whom the compliant prosthetic foot is being fabricated.

32. A method according to claim 12, wherein the target kinematic data set is a physiological data set scaled from an able-bodied subject to adjust for differences in body size and mass compared to the subject for whom the compliant prosthetic foot is being fabricated.

33. A method according to claim 12, wherein the target kinematic data set is obtained by at least one member of the group consisting of simulation, measurement of a subject, measurement from a population of subjects and scaling in magnitude from a subject(s) of a different body size and weight.

34. A method according to claim 12, wherein the compliant prosthetic foot is fabricated by at least one method selected from the group consisting of: machining; three-dimensional printing; a layup method; a water jet method; additive fabrication; subtractive fabrication; lamination; composite manufacture; injection molding; carbon fiber fabrication; extrusion; casting; molding; co-molding; carving; and vulcanization.

35. A method according to claim 12, wherein the compliant prosthetic foot is fabricated of at least one member of the group consisting of: nylon 6/6; carbon fiber; fiber glass; spring steel; titanium; plastic; an alloy of metals; a polymer; a composite; a resin; a thermoplastic; laminate; a rubber; an elastomer; a non-viscoelastic material; a viscoelastic material; and wood.

* * * * *